(12) United States Patent
Benz et al.

(10) Patent No.: US 6,984,700 B2
(45) Date of Patent: Jan. 10, 2006

(54) COMPOUNDS CONTAINING SILICON-CONTAINING GROUPS, MEDICAL DEVICES, AND METHODS

(75) Inventors: Michael Eric Benz, Ramsey, MN (US); Christopher M. Hobot, Tonka Bay, MN (US); David L. Miller, Circle Pines, MN (US); David A. Pearson, Maple Grove, MN (US); Mark A. Tapsak, San Diego, CA (US); Edward DiDomenico, Anoka, MN (US); Randall V. Sparer, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/246,807

(22) Filed: Sep. 17, 2002

(65) Prior Publication Data

US 2004/0054080 A1 Mar. 18, 2004

(51) Int. Cl.
*C08L 83/05* (2006.01)

(52) U.S. Cl. .......................... 525/474; 528/35; 528/38; 528/43; 528/68

(58) Field of Classification Search ................ 525/474; 528/35, 38, 43, 68
See application file for complete search history.

(56) References Cited

U.S. PATENT DOCUMENTS

| | | | |
|---|---|---|---|
| 4,208,506 A | * | 6/1980 | Deichert et al. ............... 528/32 |
| 4,647,643 A | | 3/1987 | Zdrahala et al. |
| 4,873,308 A | | 10/1989 | Coury et al. |
| 4,883,854 A | | 11/1989 | Coury et al. |
| 5,040,544 A | | 8/1991 | Lessar et al. |
| 5,147,725 A | | 9/1992 | Pinchuk |
| 5,238,006 A | | 8/1993 | Markowitz |
| 5,375,609 A | | 12/1994 | Molacek et al. |
| 5,480,421 A | | 1/1996 | Otten |
| 5,561,210 A | | 10/1996 | Roy |
| 5,663,245 A | | 9/1997 | Kennedy et al. |
| 5,736,251 A | | 4/1998 | Pinchuk |
| 5,986,034 A | | 11/1999 | DiDomenico et al. |
| 6,111,052 A | | 8/2000 | DiDomenico et al. |
| 6,149,678 A | | 11/2000 | DiDomenico et al. |
| 6,252,101 B1 | | 6/2001 | Herzig et al. |
| 6,313,254 B1 | | 11/2001 | Meijs et al. |
| 6,420,452 B1 | | 7/2002 | Gunatillake et al. |
| 2002/0028901 A1 | | 3/2002 | Gunatillake et al. |
| 2003/0125499 A1 | | 7/2003 | Benz et al. |

FOREIGN PATENT DOCUMENTS

| | | |
|---|---|---|
| EP | 0 661 332 A | 7/1995 |
| EP | 0 940 405 A | 9/1999 |
| JP | 2002128856 A | 5/2002 |
| WO | WO 97/16467 | 5/1997 |
| WO | WO 98/05701 | 2/1998 |
| WO | WO 98/50086 A | 11/1998 |
| WO | WO 98/54242 | 12/1998 |
| WO | WO 99/03863 | 1/1999 |
| WO | WO 99/50327 A | 10/1999 |
| WO | WO 00/64971 A | 11/2000 |
| WO | WO 01/07499 A | 2/2001 |
| WO | 02/053612 | * 7/2002 |

OTHER PUBLICATIONS

Schwendeman et al., "Precisely Placed Gem–Dimethyl Branching in ADMET Polyethylene," Abstract from poster, Spring National American Chemical Society meeting, Orlando, FL, Apr. 7–11, 2002, *Polymer Preprints*, 2002, 43(1):280.

Schwendeman et al., "Amorphous Telechelic Hydrocarbon Diols by ADMET," Abstract from poster, Spring National American Chemical Society meeting, Orlando, FL, Apr. 7–11, 2002, *Polymer Preprints*, 2002, 43(1):282.

Hoffman et al., "Safety and Intracardiac Function of a Silicone–Polyurethane Elastomer Designed for Vascular Use," *Clin. Mater.*, 1993;13(1–4):95–100.

Pinchuk et al., "The Use of Silicone/Polyurethane Graft Polymers as a Means of Eliminating Surface Cracking of Polyurethane Prostheses," *J. Biomater. Appl.*, Oct. 1988;3(2):260–296.

Pinchuk et al., "Polyurethane/Silicone Composites as Materials for Long–Term Implant in the Human Body," Int. SAMPE Tech. Conf., 1990, 22(Adv. Mater.), 133–144.

Pinchuk et al., "Polyurethane/Silicone Composites for Long–Term Implant in the Human Body," 49$^{th}$ Annu. Tech. Conf.—Soc. Plast. Eng., 1991; pp. 1802–1804.

Schwendeman et al., "Gem–Dimethyl Branching in ADMET Polyethylene," Abstract from poster presented at the International Symposium for Olefin Metathesis (ISOM), Cambridge, MA (Aug. 5–7, 2001).

Coury et al., "Biomedical Uses of Polyurethanes," in *Advances in Urethane Science and Technology*, 9:130–168, edited by Frisch et al., Technomic Publishing Co., Lancaster, PA (1984).

* cited by examiner

*Primary Examiner*—Kuo-Liang Peng
(74) *Attorney, Agent, or Firm*—Mueting, Raasch & Gebhardt, P.A.

(57) ABSTRACT

Compounds that include silicon-containing groups, and optionally urethane groups, urea groups, or combinations thereof (i.e., polyurethanes, polyureas, or polyurethane-ureas), as well as materials and methods for making such compounds.

29 Claims, No Drawings

COMPOUNDS CONTAINING SILICON-CONTAINING GROUPS, MEDICAL DEVICES, AND METHODS

FIELD OF THE INVENTION

This invention relates to compounds containing silicon-containing groups, preferably such compounds are polymers containing urethane and/or urea groups, particularly elastomers. Such materials are particularly useful as biomaterials in medical devices.

BACKGROUND OF THE INVENTION

The chemistry of polyurethanes and/or polyureas is extensive and well developed. Typically, polyurethanes and/or polyureas are made by a process in which a polyisocyanate is reacted with a molecule having at least two functional groups reactive with the polyisocyanate, such as a polyol or polyamine. The resulting polymer can be further reacted with a chain extender, such as a diol or diamine, for example. The polyol or polyamine is typically a polyester, polyether, or polycarbonate polyol or polyamine, for example.

Polyurethanes and/or polyureas can be tailored to produce a range of products from soft and flexible to hard and rigid. They can be extruded, injection molded, compression molded, and solution spun, for example. Thus, polyurethanes and polyureas, particularly polyurethanes, are important biomedical polymers, and are used in implantable devices such as artificial hearts, cardiovascular catheters, pacemaker lead insulation, etc.

Commercially available polyurethanes used for implantable applications include BIOSPAN segmented polyurethanes, manufactured by Polymer Technology Group of Berkeley, Calif., PELLETHANE segmented polyurethanes, sold by Dow Chemical, Midland, Mich., and TECOFLEX segmented polyurethanes sold by Thermedics, Inc., Woburn, Mass. Polyurethanes are described in the article "Biomedical Uses of Polyurethanes," by Coury et al., in *Advances in Urethane Science and Technology*, 9, 130–168, edited by Kurt C. Frisch and Daniel Klempner, Technomic Publishing Co., Lancaster, Pa. (1984). Typically, polyether polyurethanes exhibit more biostability than polyester polyurethanes and polycarbonate polyurethanes, as these are more susceptible to hydrolysis. Thus, polyether polyurethanes are generally preferred biopolymers.

Polyether polyurethane elastomers, such as PELLETHANE 2363-80A (P80A) and 2363-55D (P55D), which are prepared from polytetramethylene ether glycol (PTMEG) and methylene bis(diisocyanatobenzene) (MDI) extended with 1,4-butanediol, are widely used for implantable cardiac pacing leads. Pacing leads are electrodes that carry stimuli to tissues and biologic signals back to implanted pulse generators. The use of polyether polyurethane elastomers as insulation on such leads has provided significant advantage over silicone rubber, primarily because of the higher tensile strength of the polyurethanes.

There is some problem, however, with biodegradation of polyether polyurethane insulation, which can cause failure. Polyether polyurethanes are susceptible to oxidation in the body, particularly in areas that are under stress. When oxidized, polyether polyurethane elastomers can lose strength and can form cracks, which might eventually breach the insulation. This, thereby, can allow bodily fluids to enter the lead and form a short between the lead wire and the implantable pulse generator (IPG). It is believed that the ether linkages degrade, perhaps due to metal ion catalyzed oxidative attack at stress points in the material.

One approach to solving this problem has been to coat the conductive wire of the lead. Another approach has been to add an antioxidant to the polyurethane. Yet another approach has been to develop new polyurethanes that are more resistant to oxidative attack. Such polyurethanes include only segments that are resistant to metal induced oxidation, such as hydrocarbon- and carbonate-containing segments. For example, polyurethanes that are substantially free of ether and ester linkages have been developed. This includes the segmented aliphatic polyurethanes of U.S. Pat. No. 4,873,308 (Coury et al.). Another approach has been to include a sacrificial moiety (preferably in the polymer backbone) that preferentially oxidizes relative to all other moieties in the polymer, which upon oxidation provides increased tensile strength relative to the polymer prior to oxidation. This is disclosed in U.S. Pat. No. 5,986,034 (DiDomenico et al.), U.S. Pat. No. 6,111,052 (DiDomenico et al.), and U.S. Pat. No. 6,149,678 (DiDomenico et al.).

Although such materials produce more stable implantable devices than polyether polyurethanes, there is still a need for biostable polymers, particularly polyurethanes suitable for use as insulation on pacing leads.

SUMMARY OF THE INVENTION

The present invention relates to compounds, preferably polymers, that include silicon-containing groups. The silicon-containing groups are typically silane- and/or siloxane-containing groups. Particularly preferred polymers include urethane groups, urea groups, or combinations thereof (i.e., polyurethanes, polyureas, or polyurethane-ureas). Polymers of the present invention may be random, alternating, block, star block, segmented, or combinations thereof. Preferably, the polymer is a segmented polyurethane. Certain embodiments of the polymers of the present invention can be used as biomaterials in medical devices. Preferred polymers are also preferably substantially free of ester, ether, and carbonate linkages.

The present invention also provides a polymer, and a medical device that incorporates such polymer, wherein the polymer is prepared from a compound (typically a polymeric starting material) of the formula (Formula I):

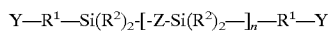

wherein: each Y is independently OH or $NR^4H$; n=2 or more; each $R^1$ is independently a straight chain or branched alkylene group (typically referred to as a divalent saturated aliphatic group) optionally including heteroatoms; each $R^2$ is independently a saturated or unsaturated aliphatic group, an aromatic group, or combinations thereof, optionally including heteroatoms (typically referred to as a monovalent group); Z is oxygen or $R^3$ wherein each $R^3$ is independently a straight chain alkylene group, a phenylene group, or a straight chain or branched alkyl substituted phenylene group, wherein each $R^3$ optionally includes heteroatoms; and each $R^4$ is independently H or a saturated or unsaturated aliphatic group, an aromatic group, or combinations thereof; with the proviso that at least one of the Z groups is oxygen and at least one of the Z groups is $R^3$ (preferably, every other Z is oxygen); and with the proviso that $R^1$ does not include urethane groups when Y is OH (although $R^1$ does become part of urethane linkages).

Polymers of the present invention thereby include groups of the formula (Formula II):

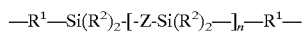

wherein Y, n, $R^1$, $R^2$, Z, and $R^4$ are as defined herein.

Also provided is a compound of the formula (Formula I):

$$Y-R^1-Si(R^2)_2-[-Z-Si(R^2)_2-]_n-R^1-Y$$

wherein: each Y is independently OH or $NR^4H$; n=2 or more; each $R^1$ is independently a straight chain or branched alkylene group optionally including heteroatoms; each $R^2$ is independently a saturated or unsaturated aliphatic group, an aromatic group, or combinations thereof, optionally including heteroatoms; Z is oxygen or $R^3$, wherein each $R^3$ is independently a straight chain alkylene group, a phenylene group, or a straight chain or branched alkyl substituted phenylene group, wherein each $R^3$ optionally includes heteroatoms; and each $R^4$ is independently H or a saturated or unsaturated aliphatic group, an aromatic group, or combinations thereof; with the proviso that at least one of the Z groups is oxygen and at least one of the Z groups is $R^3$ (preferably, every other Z is oxygen); and with the proviso that $R^1$ does not include urethane groups.

It should be understood that in the above formulas, the repeat unit $-Z-Si(R^2)_2-$ can vary within any one molecule. That is, in addition to each of the $R^2$ groups being the same or different within each $Si(R^2)_2$ group, each of the $-Z-Si(R^2)_2-$ groups can be the same or different in any one molecule.

As written, the formulas provided herein (for both the resultant polymers and the polymeric starting materials) encompass alternating, random, block, star block, segmented copolymers, and combinations thereof (e.g., wherein certain portions of the molecule are alternating and certain portions are random). With respect to star block copolymers, it should be understood that the polymeric segments described herein could form at least a part of one or more arms of the star, although the segment itself would not necessarily include the core branch point of the star.

Methods of preparation of such polymers and compounds are also provided. In one embodiment of making a segmented polymer, the method includes combining a polyisocyanate with a compound of Formula I.

As used herein, the terms "a," "an," "one or more," and "at least one" are used interchangeably.

As used herein, the term "aliphatic group" means a saturated or unsaturated linear (i.e., straight chain), cyclic (i.e., cycloaliphatic), or branched organic hydrocarbon group. This term is used to encompass alkyl (e.g., $-CH_3$, which is considered a "monovalent" group) (or alkylene if within a chain such as $-CH_2-$, which is considered a "divalent" group), alkenyl (or alkenylene if within a chain), and alkynyl (or alkynylene if within a chain) groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "aromatic group" or "aryl group" means a mono- or polynuclear aromatic organic hydrocarbon group. These hydrocarbon groups may be substituted with heteroatoms, which can be in the form of functional groups. The term "heteroatom" means an element other than carbon (e.g., nitrogen, oxygen, sulfur, chlorine, etc.).

As used herein, a "biomaterial" may be defined as a material that is substantially insoluble in body fluids and tissues and that is designed and constructed to be placed in or onto the body or to contact fluid or tissue of the body.

Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body. A "biostable" material is one that is not broken down by the body, whereas a "biocompatible" material is one that is not rejected by the body.

As used herein, a "medical device" may be defined as a device that has surfaces that contact blood or other bodily tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as vascular grafts, stents, electrical stimulation leads, heart valves, orthopedic devices, catheters, shunts, sensors, replacement devices for nucleus pulposus, cochlear or middle ear implants, intraocular lenses, and the like.

DETAILED DESCRIPTION OF ILLUSTRATIVE EMBODIMENTS OF THE INVENTION

The present invention provides polymers (preferably, segmented polyurethanes), compounds used to prepare such polymers (preferably, these form the soft segments of segmented polymers), and medical devices that include such polymers (preferably, biomaterials). Preferably, the polymers are generally resistant to oxidation and/or hydrolysis, particularly with respect to their backbones, as opposed to their side chains.

The polymers include one or more silicon-containing groups. These silicon-containing groups are of the formula $-Z-Si(R^2)_2-$ wherein Z is oxygen (thereby forming a siloxane group) or is $R^3$ (thereby forming a silane group). Each $R^3$ may be the same or different (i.e., is independently) and is a straight chain alkylene group, a phenylene group, or a straight chain or branched alkyl substituted pheylene group, wherein each $R^3$ optionally includes heteroatoms (which may be in the chain of the organic group or pendant therefrom as in a functional group). In any one compound, at least one of the Z groups is oxygen and at least one of the Z groups is an $R^3$ group. For certain embodiments, the Z groups are alternating with every "even" numbered Z group being an oxygen (i.e., every other Z is oxygen).

Polymers of the present invention are prepared from a compound of the formula (Formula I):

$$Y-R^1-Si(R^2)_2-[-Z-Si(R^2)_2-]_n-R^1-Y$$

wherein: each Y is independently OH or $NR^4H$; n=2 or more; each $R^1$ is independently a straight chain or branched alkylene group optionally including heteroatoms; each $R^2$ is independently a saturated or unsaturated aliphatic group, an aromatic group, or combinations thereof, optionally including heteroatoms; Z is as defined above; and each $R^4$ is independently H or a saturated or unsaturated aliphatic group, an aromatic group, or combinations thereof.

Polymers of the present invention thereby include groups of the formula (Formula II):

$$-R^1-Si(R^2)_2-[-Z-Si(R^2)_2-]_n-R^1-$$

wherein n, $R^1$, $R^2$, and Z are as defined herein.

Polymers of the present invention can be used in medical devices as well as nonmedical devices. Preferably, they are used in medical devices and are suitable as biomaterials. Examples of medical devices are listed above. Examples of nonmedical devices include foams, insulation, clothing, footwear, paints, coatings, adhesives, building construction materials, etc.

The polymers suitable for forming biomaterials for use in medical devices according to the present invention include silicon-containing groups, and are preferably polyurethanes, polyureas, or polyurethane-ureas. These polymers can vary from hard and rigid to soft and flexible. Preferably, the polymers are elastomers. An "elastomer" is a polymer that is capable of being stretched to approximately twice its original length and retracting to approximately its original length upon release.

Polymers of the present invention can be or copolymers, although preferably, they are random, alternating, block, star block, segmented copolymers, or combinations thereof. Most preferably, the polymers are segmented copolymers (i.e., containing a multiplicity of both hard and soft domains or segments on any polymer chain) and are comprised substantially of alternating relatively soft segments and relatively hard segments.

For segmented polymers, either the hard or the soft segments, or both, can include a silicon-containing moiety, thereby providing a polymer that has reduced susceptibility to oxidation and/or hydrolysis, at least with respect to the polymer backbone. As used herein, a "hard" segment is one that is either crystalline at use temperature or amorphous with a glass transition temperature above use temperature (i.e., glassy), and a "soft" segment is one that is amorphous with a glass transition temperature below use temperature (i.e., rubbery). A crystalline or glassy moiety or hard segment is one that adds considerable strength and higher modulus to the polymer. Similarly, a rubbery moiety or soft segment is one that adds flexibility and lower modulus, but may add strength particularly if it undergoes strain crystallization, for example. The random or alternating soft and hard segments are linked by urethane and/or urea groups and the polymers may be terminated by hydroxyl, amine, and/or isocyanate groups.

As used herein, a "crystalline" material or segment is one that has ordered domains. A "noncrystalline" material or segment is one that is amorphous (a noncrystalline material may be glassy or rubbery). A "strain crystallizing" material is one that forms ordered domains when a strain or mechanical force is applied.

An example of a medical device for which the polymers are particularly well suited is a medical electrical lead, such as a cardiac pacing lead, a neurostimulation lead, etc. Examples of such leads are disclosed, for example, in U.S. Pat. No. 5,040,544 (Lessar et al.), U.S. Pat. No. 5,375,609 (Molacek et al.), U.S. Pat. No. 5,480,421 (Otten), and U.S. Pat. No. 5,238,006 (Markowitz).

Polymers and Methods of Preparation

A wide variety of polymers are provided by the present invention. They can be or random, alternating, block, star block, segmented copolymers (or combinations thereof, preferably they are copolymers (including terpolymers, tetrapolymers), that can include olefins, amides, esters, imides, epoxies, ureas, urethanes, carbonates, sulfones, ethers, acetals, phosphonates, and the like. These include silicon-containing groups of the formula —O—Si($R^2$)$_2$— (siloxane groups) or —$R^3$—Si($R^2$)$_2$— (silane groups). Such polymers can be prepared using a variety of techniques from polymerizable compounds (e.g., monomers, oligomers, or polymers) containing such silicon-containing groups. Such compounds include dienes, diols, diamines, or combinations thereof, for example.

Although certain preferred polymers are described herein, the polymers used to form the preferred biomaterials in the medical devices of the present invention can be a wide variety of polymers that include urethane groups, urea groups, or combinations thereof. Such polymers are prepared from isocyanate-containing compounds, such as polyisocyanates (preferably diisocyanates) and compounds having at least two functional groups reactive with the isocyanate groups, such as polyols and/or polyamines (preferably diols and/or diamines). Any of these reactants can include a silicon-containing group (preferably in the polymer backbone), although preferably a silicon-containing moiety is provided by the diols and/or diamines of Formula I.

The presence of the silicon-containing moiety provides a polymer that is typically more resistant to oxidative and/or hydrolytic degradation but still has a relatively low glass transition temperature (Tg). Furthermore, preferably, both the hard and soft segments are themselves substantially ether-free, ester-free, and carbonate-free polyurethanes, polyureas, or combinations thereof. As stated above, the silicon-containing groups are of the formula -Z-Si($R^2$)$_2$— wherein Z is oxygen (thereby forming a siloxane group) or is $R^3$ (thereby forming a silane group).

In one embodiment, particularly preferred polymers also include one or more urethane groups, urea groups, or combinations thereof (preferably, just urethane groups). In another embodiment, particularly preferred polymers are copolymers (i.e., prepared from two or more monomers, including terpolymers or tetrapolymers). Thus, the present invention provides polymers with the silicon-containing groups randomly distributed or ordered in blocks or segments.

Polymers of the present invention can be linear, branched, or crosslinked. This can be done using polyfunctional isocyanates or polyols (e.g., diols, triols, etc.) or using compounds having unsaturation or other functional groups (e.g., thiols) in one or more monomers with radiation crosslinking. Such methods are well known to those of skill in the art.

Preferably, such polymers (and the compounds used to make them) have substantially no tertiary carbons in the main chain (i.e., backbone).

A preferred source of the group of the formula —[—($R^1$)$_n$-(-Z-($R^2$)$_m$—)$_p$—(—Si(R)$_2$—V$_r$—)$_s$—]$_q$— is a compound (typically a polymeric starting compound) of the formula (Formula I):

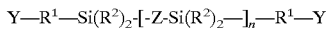

wherein: each Y is independently OH or $NR^4H$; n=2 or more; each $R^1$ is independently a straight chain or branched alkylene group optionally including heteroatoms; each $R^2$ is independently a saturated or unsaturated aliphatic group, an aromatic group, or combinations thereof, optionally including heteroatoms; Z is oxygen or $R^3$, wherein each $R^3$ is independently a straight chain alkylene group, a phenylene group, or a straight chain or branched alkyl substituted phenylene group, wherein each $R^3$ optionally includes heteroatoms; and each $R^4$ is independently H or a saturated of unsaturated aliphatic group, an aromatic group, or combinations thereof; with the proviso that at least one of the Z groups is oxygen and at least one of the Z groups is $R^3$; and with the proviso that $R^1$ does not include urethane groups when Y is OH.

It should be understood that in Formula I, the repeat unit -Z-Si($R^2$)$_2$— can vary within any one molecule. That is, in addition to each of the $R^2$ groups being the same or different within each $Si(R^2)_2$ group, the $-Z-Si(R^2)_2-$ groups can be the same or different in any one molecule. The value for "n" is an average value. Preferably, n is 1 to 50, and more preferably, n is 1 to 20.

The $R^1$, $R^2$, and $R^3$ groups are selected such that the number average molecular weight of a polymeric starting material of the present invention is preferably no greater than about 100,000 grams per mole (g/mol or Daltons), more preferably, no greater than about 5000 g/mol, and most preferably no greater than about 1500 g/mol. Preferably, the number average molecular weight of the polymeric starting material is at least about 500 g/mol.

The number average molecular weight of the resultant polymer (without crosslinking) of the present invention is preferably no greater than about 100,000,000 g/mol, which is desirable for melt processing of the polymer More preferably, the number average molecular weight of the resultant polymer (without crosslinking) of the present invention is no greater than about 500,000 g/mol. Preferably, the number average molecular weight of the polymer (without crosslinking) is at least about 20,000 g/mol.

Each $R^1$ is independently a straight chain or branched alkylene group (i.e., a divalent saturated aliphatic group) optionally including heteroatoms, such as nitrogen, oxygen, phosphorus, sulfur, and halogen. The heteroatoms can be in the backbone of the polymer or pendant therefrom, and they can form functional groups (e.g., carbonyl). Preferably, $R^1$ does not include heteroatoms. More preferably, each $R^1$ is independently a straight chain or branched alkylene group includes 20 carbon atoms or less. Most preferably, each $R^1$ is independently a straight chain or branched (C3–C20) alkylene group.

The $R^2$ groups on the silicon atoms are selected such that the ultimate product (e.g., a segmented polyurethane polymer) has the following properties relative to a polymer without the silicon-containing groups: greater chain flexibility; less susceptibility to oxidation and hydrolysis; and/or greater ability to modify the polymers using functional groups within the R groups.

Although the silicon-containing groups reduce the susceptibility of the polymeric starting material and the ultimate polymer to oxidation or hydrolysis, the $R^2$ groups could themselves be susceptible to oxidation or hydrolysis as long as the main chain (i.e., the backbone) is not generally susceptible to such reactions.

Each $R^2$ is independently a monovalent saturated or unsaturated aliphatic group, an aromatic group, or combinations thereof, optionally including heteroatoms. Preferably, the $R^2$ groups are each independently an alkyl group, an aryl group, or combinations thereof. More preferably, the $R^2$ groups are each independently an alkyl group, a phenyl group, or an alkyl substituted phenyl group. Even more preferably, the $R^2$ groups are each independently a straight chain or branched alkyl group (preferably having 20 carbon atoms or less), a phenyl group, or a straight chain or branched alkyl substituted phenyl group (preferably having 20 carbon atoms or less, and more preferably 6 carbon atoms or less, in the alkyl substituent). Most preferably, the $R^2$ groups are each independently a straight chain or branched (C1–C3)alkyl group (preferably without heteroatoms).

Optionally, the $R^2$ groups can include heteroatoms, such as nitrogen, oxygen, phosphorus, sulfur, and halogen. These could be in the chain of the organic group or pendant therefrom in the form of functional groups, as long as the polymer is generally resistant to oxidation and/or hydrolysis, particularly with respect to its backbone, as opposed to its side chains. Such heteroatom-containing groups (e.g., functional groups) include, for example, an alcohol, ether, acetoxy, ester, aldehyde, acrylate, amine, amide, imine, imide, and nitrile, whether they be protected or unprotected.

Each $R^3$ is independently a straight chain alkylene group, a phenylene group, or a straight chain or branched alkyl substituted phenylene group, wherein each $R^3$ group optionally includes heteroatoms. Preferably, each $R^3$ is independently a straight chain alkylene group. Preferably, $R^3$ does not include heteroatoms. More preferably, each $R^3$ group includes 20 carbon atoms or less, even more preferably 12 carbon atoms or less, and most preferably 10 carbon atoms or less. More preferably, each $R^3$ group includes at least 1 carbon atom, more preferably, at least 4 carbon atoms, and most preferably at least 6 carbon atoms. Alternatively, each alkyl substituent on the phenylene group independently and preferably includes 20 carbon atoms or less, even more preferably 12 carbon atoms or less, and most preferably 10 carbon atoms or less. More preferably, each alkyl substituent on the phenylene group independently and preferably includes at least 1 carbon atom, more preferably, at least 4 carbon atoms, and most preferably at least 6 carbon atoms.

Each $R^4$ is independently H or a saturated or unsaturated aliphatic group, an aromatic group, or combinations thereof. Preferably, each $R^4$ is independently hydrogen, a straight chain alkyl group, an aryl group, or combinations thereof. More preferably, each $R^4$ is independently hydrogen or a straight chain alkyl group. Preferably, $R^4$ is hydrogen or an organic group that includes at least one carbon atom. Preferably, $R^4$ is an organic group that includes no more than 100 carbon atoms, more preferably no more than 50 carbon atoms, even more preferably no more than 20 carbon atoms, and most preferably no more than 4 carbon atoms. Most preferably, $R^4$ is hydrogen.

Preferably, the Y groups are OH or $NH_2$. More preferably, the Y groups are both OH.

The polymers of the present invention can be prepared using standard techniques. Certain polymers can be made using one or more of the compounds of Formula I.

For example, if Y in Formula I is an amine ($NR^4H$), one could react those amines with di-, tri- or poly(acids), di-, tri, or poly(acyl chlorides), or with cyclic amides (lactams) to form poly(amides). Alternatively, one could react those amines with di-, tri- or poly(anhydrides) to make poly (imides). Alternatively, one could react those amines with glycidyl-containing compounds to form epoxies.

If Y in Formula I is hydroxyl (OH), one could react those hydroxyl groups with di-, tri-, or poly(acids), di-, tri-, or poly(acyl chlorides), or with cyclic esters (lactones) to form poly(esters). Alternatively, one could react those hydroxyl groups with vinyl ether-containing compounds to make poly(acetals). Alternatively, one could react those hydroxyls with sodium hydroxide to form sodium salts, and further react those salts with phosgene to form poly(carbonates). Reacting those sodium salts with other alkyl halide containing moieties can lead to poly(sulfones) and poly(phosphates) and poly(phosphonates).

Typically, the preferred urethane- and/or urea-containing polymers are made using polyisocyanates and one or more compounds of Formula I. It should be understood, however, that diols or diamines that do not contain such silicon-containing moieties can also be used to prepare the urethane- and/or urea-containing polymers (particularly the soft segments of the polymers) of the present invention, as long as the resultant polymer includes at least some silicon-containing moieties either from diols or diamines or other reactants. Also, other polyols and/or polyamines can be used, including polyester, polyether, and polycarbonate polyols, for example, although such polyols are less preferred because they produce less biostable materials. Furthermore, the polyols and polyamines can be aliphatic (including cycloaliphatic) or aromatic, including heterocyclic compounds, or combinations thereof.

Examples of suitable polyols (typically diols) include those commercially available under the trade designation POLYMEG and other polyethers such as polyethylene glycol and polypropylene oxide, polybutadiene diol, dimer diol (e.g., that commercially available under the trade designation DIMEROL (from Pripol 2033 from Unichema, North America of Chicago, Ill.), polyester-based diols such as those commercially available as STEPANPOL (from Stepan Corp., Northfield, Ill.), CAPA (a polycaprolactone diol from Solvay, Warrington, Cheshire, United Kingdom), TERATE (from Kosa, Houston, Tex.), poly(ethylene adipate) diol, poly(ethylene succinate) diol, poly(1,4-butanediol adipate) diol, poly(caprolactone) diol, poly(hexamethylene phthalate) diol, and poly(1,6-hexamethylene adipate) diol, as well as polycarbonate-based diols such as poly (hexamethylene carbonate) diol.

Other polyols can be used as chain extenders in the preparation of polymers, as is conventionally done in the preparation of polyurethanes, for example. Chain extenders are used to provide hard segments. Examples of suitable chain extenders include 1,10-decanediol, 1,12-dodecanediol, 9-hydroxymethyl octadecanol, cyclohexane-1,4-diol, cyclohexane-1,4-bis(methanol), cyclohexane-1,2-bis(methanol), ethylene glycol, diethylene glycol, 1,3-propylene glycol, dipropylene glycol, 1,2-propylene glycol, trimethylene glycol, 1,2-butylene glycol, 1,3-butanediol, 2,3-butanediol, 1,4-butanediol, 1,5-pentanediol, 1,6-hexanediol, 1,2-hexylene glycol, 1,2-cyclohexanediol, 2-butene-1,4-diol, 1,4-cyclohexanedimethanol, 2,4-dimethyl-2,4-pentanediol, 2-methyl-2,4-pentanediol, 1,2,4-butanetriol, 2-ethyl-2-(hydroxymethyl)-1,3-propanediol, glycerol, 2-(hydroxymethyl)-1,3-propanediol, neopentyl glycol, pentaerythritol, and the like. Other chain extenders are described in International Publication No. WO 99/03863.

Examples of suitable polyamines (typically diamines) include ethylenediamine, 1,4-diaminobutane, 1,10-diaminodecane, 1,12-diaminododecane, 1,8-diaminooctane, 1,2-diaminopropane, 1,3-diaminopropane, tris(2-aminoethyl)amine, lysine ethyl ester, and the like.

Examples of suitable mixed alcohols/amines include 5-amino-1-pentanol, 6-amino-1-hexanol, 4-amino-1-butanol, 4-aminophenethyl alcohol, ethanolamine, and the like.

Suitable isocyanate-containing compounds for preparation of polyurethanes, polyureas, or polyurethanes-ureas, are typically aliphatic, cycloaliphatic, aromatic, and heterocyclic (or combinations thereof) polyisocyanates. In addition to the isocyanate groups they can include other functional groups such as biuret, urea, allophanate, uretidine dione (i.e., isocyanate dimer), and isocyanurate, etc., that are typically used in biomaterials. Suitable examples of polyisocyanates include 4,4'-diisocyanatodiphenyl methane (MDI), 4,4'-diisocyanatodicyclohexyl methane (HMDI), cyclohexane-1, 4-diisocyanate, cyclohexane-1,2-diisocyanate, isophorone diisocyanate, tolylene diisocyanates, naphthylene diisocyanates, benzene-1,4-diisocyanate, xylene diisocyanates, trans-1,4-cyclohexylene diisocyanate, 1,4-diisocyanatobutane, 1,12-diisocyanatododecane, 1,6-diisocyanatohexane, 1,5-diisocyanato-2-methylpentane, 4,4'-methylenebis(cyclohexyl isocyanate), 4,4'-methylenebis(2,6-diethyphenyl isocyanate), 4,4'-methylenebis(phenyl isocyanate), 1,3-phenylene diisocyanate, poly((phenyl isocyanate)-co-formaldehyde), tolylene-2,4-diisocyanate, tolylene-2,6-diisocyanate, dimer diisocyanate, as well as polyisocyanates available under the trade designations DESMODUR RC, DESMODUR RE, DESMODUR RFE, and DESMODUR RN from Bayer, and the like.

The relatively hard segments of the polymers of the present invention are preferably fabricated from short to medium chain diisocyanates and short to medium chain diols or diamines, all of which preferably have molecular weights of less than about 1000 grams per mole. Appropriate short to medium chain diols, diamines, and diisocyanates include straight chain, branched, and cyclic aliphatics, although aromatics can also be used. Examples of diols and diamines useful in these more rigid segments include both the short and medium chain diols or diamines discussed above.

In addition to the polymers described herein, biomaterials of the invention can also include a variety of additives. These include, antioxidants, colorants, processing lubricants, stabilizers, imaging enhancers, fillers, and the like.

Starting Materials and Methods of Preparation

The compounds of Formula I above can be made by the synthetic route described in the Examples Section. This typically involves the reaction of tetramethyldisiloxane (TMDS) and a hydrocarbon diene in an inert atmosphere using a catalyst such as platinum divinyl TMDS. Molecular weights can be targeted by the ratio of the two components (e.g., 3:2 TMDS to 1,7-octadiene would give approximately 620 Mn (number average molecular weight) with hydride termination). A protected hydroxyl or amine group can then be added through reaction of another alkene terminated molecule to the hydride end groups. Allyloxytrimethylsilane or allylaminotrimethysilane are examples of protected hydroxyl and amine that can be attached through the allyl group to the hydride. The hydroxyl or amine is then deprotected. Water will deprotect the aminotrimethylsilane. Citric acid is one way to deprotect the oxytrimethylsilane.

The invention has been described with reference to various specific and preferred embodiments and will be further described by reference to the following detailed examples. It is understood, however, that there are many extensions, variations, and modification on the basic theme of the present invention beyond that shown in the examples and detailed description, which are within the spirit and scope of the present invention.

EXAMPLES

Materials: 10-Undecen-1-yl acetate was purchased from Bedoukian Research Incorporated (Danbury, Conn.). Hydrolsilylation catalyst (platinum (divinyltetramethyldisiloxane), containing 2–3% platinum in xylenes), 1,1,3,3-tetramethyldisiloxane (TMDS), and 1,8-bis(chlorodimethyl)octane were purchased from United Chemical Technologies (Bristol, Pa.). 1,4-Butanediol was purchased from Mitsubishi Chemical America, Inc. (White Plains, N.Y.). 4,4'-methylenebis(phenylisocyanate) (tradename Mondur M, flaked) was purchased from Bayer Corporation (Pittsburgh, Pa.). The remaining reagents may be purchased from Aldrich Chemical Company, Incorporated (Milwaukee, Wis.).

Example 1

Synthesis of a Polyurethane/Urea from an Aminotelechelic Alternating Siloxane-Hydrocarbon Polymer Part 1: Synthesis of a 1500 Mn aminotelechelic alternating siloxane-hydrocarbon polymer.

A 3-neck round-bottomed flask was fitted with thermometer and adapter, magnetic stirring mechanism, water bath, cold-water condenser, pressure equalized addition funnel, glycerol bubbler and trap, and stopper. Nitrogen blanketing was used. 1,1,3,3-Tetramethyldisiloxane (TMDS) was added to the flask. In the addition funnel was placed 1,7-octadiene. The molar ratio of TMDS to 1,7-octadiene was 7:6. Catalyst (platinum(divinyltetramethyldisiloxane)) was added dropwise at various points of the reaction as the 1,7-octadiene was added dropwise, being careful to control the exotherm of the reaction. The polymer was heated to 80° C. for an additional 1.5 hours.

A one-liter 3-neck round-bottomed flask was fitted with thermometer and adapter, magnetic stirring mechanism, heating unit, cold-water condenser, pressure equalized addition funnel, glycerol bubbler and trap, and stopper. Nitrogen blanketing was used. N-(Trimethylsilyl)allylamine (115.15 gm) was added to the flask. In the addition funnel was placed 342.97 grams (gm) of the hydride terminated disiloxane-hydrocarbon polymer synthesized above. The flask was heated to 95° C., then the polymer was added over about one hour keeping the temperature between 86° C. and 96° C. Next, water (55 milliliters (ml)) and toluene (200 ml) were added to the flask. The water was separated and the toluene solution washed again with water. The polymer was filtered through AMBERLITE IRC-718 ion exchange resin, rotary evaporated, then dried in a vacuum oven.

Part 2: Synthesis of a polyurethane/urea using the aminotelechelic alternating disiloxane-hydrocarbon polymer of Part 1.

A 250-ml 3-neck round-bottomed flask was fitted with a Dean-Stark trap, condenser, nitrogen blanket, thermocouple, and stirring mechanism. A mixture of 20 ml N,N-dimethylacetamide (DMAC), 80 ml o-xylene and 20 ml cyclohexane was heated in the flask until 20 ml of the mixture was distilled. The flask was cooled, sealed and transferred to an inert atmosphere glovebox. The solvent mixture was then heated to 50° C., and 4,4'-methylenebis(phenylisocyanate) (MDI, 10.56 gm) was added to the flask. The aminotelechelic alternating disiloxane-hydrocarbon polymer of Part 1 (37.84 gm) was placed in a syringe and transferred to the inert atmosphere glovebox. 1,4-Butanediol (1.85 gm) was also placed in a syringe and transferred to the inert atmosphere glovebox. The aminotelechelic alternating disiloxane-hydrocarbon polymer of Part 1 was added to the flask over 20 minutes with the temperature of the mixture maintained between 50° C. and 69° C. After the addition was complete, the flask temperature was stabilized at about 65° C. After another 20 minutes, the 1,4-butanediol was added over 12 minutes with the temperature rising to 69° C. The mixture was hazy, so additional DMAC and xylene were added. After 90 ml DMAC and 40 ml xylene were added, the mixture cleared somewhat. A drop of dibutyltin dilaurate catalyst was added. The temperature was raised to 90° C. to complete the reaction. There was a complete lack of isocyanate peak by infrared analysis at 2272 cm$^{-1}$. Because an isocyanate-terminated polyurethane was desired, additional MDI (0.15 gm) was added. The polymer was precipitated by addition to a mixture of acetone and water, filtered through bolting cloth and dried in a vacuum oven.

Properties of the polyurethane/urea. The dried polyurethane/urea was solvent cast and heat pressed for testing of mechanical properties. The results are presented in Table 1. Tensile properties of the test specimens were determined using an Instron Testing Machine with crosshead speed of 12.7 centimeters per minute (cm/min) using a 22.67 kilogram (kg) (50 pound) load cell.

To determine the molecular weights of the polymers, samples were dissolved in tetrahydrofuran and analyzed using an Alliance high performance liquid chromatography system (Waters Technologies Corporation, Milford, Mass.). Phenomenex columns (HR4, 3, 1 and 0.5) were used (Phenomenex USA, Torrance, Calif.). Tetrahydrofuran was used as the eluent at 0.28 milliliters per minute (ml/min) and 50° C. The molecular weight values reported are relative to a polystyrene standard curve.

TABLE 1

| Property | Solvent cast polymer | Heat pressed polymer |
| --- | --- | --- |
| Hardness (Shore scale) | 80 A | |
| Ultimate tensile | 16.5 MPa (2400 psi) | 9 MPa (1300 psi) |
| Elongation at break | 460% | 410% |
| Young's modulus | 24.8 MPa (3600 psi) | 22.8 MPa (3300 psi) |
| $M_n$ | 30800 g/mol | 27000 g/mol |
| $M_w$ | 113000 g/mol | 67300 g/mol |

This data indicates that the solvent-cast polymer had better tensile properties. The remaining properties are similar for the two polymers.

Example 2

Synthesis of a Polyurethane/Urea from an Aminotelechelic Alternating Siloxane-Hydrocarbon Polymer Part 1: Synthesis of a 1500 Mn aminotelechelic alternating disiloxane-hydrocarbon polymer.

A 2000-ml 3-neck round-bottomed flask was fitted with thermometer and adapter, magnetic stirring mechanism, water bath, cold-water condenser, pressure equalized addition funnel, glycerol bubbler and trap, and stopper. Nitrogen blanketing was used. 1,1,3,3-Tetramethyldisiloxane (393.97 gm) was added to the flask. In the addition funnel was placed 1,5-hexadiene (206.51 gm). Catalyst (platinum (divinyltetramethyldisiloxane)) was added dropwise at various points of the reaction as the diene was added dropwise, being careful to control the exotherm of the reaction. The entire reaction took about 3 hours, starting at room temperature and reaching a maximum of 76° C. The polymer was heated to 80° C. for additional time (about 1.5 hours).

A 1000-ml 3-neck round-bottomed flask was fitted with thermometer and adapter, magnetic stirring mechanism, heating unit, cold-water condenser, pressure equalized addition funnel, glycerol bubbler and trap, and stopper. Nitrogen blanketing was used. N-(Trimethylsilyl)allylamine (119.30 gm) was added to the flask. In the addition funnel was placed a portion of the hydride terminated silicone-hydrocarbon from above (352.82 gm). The flask was heated to 95° C., then the polymer was added over about one-half hour keeping the temperature between 88° C. and 95° C. Water was added (60 ml) and toluene (200 ml). The water was separated and the toluene solution washed again with water. The polymer was filtered through a Whatman #2 filter and AMBERLITE IRC-718 ion exchange resin, and then dried in a vacuum oven.

Part 2: Synthesis of a polyurethane/urea from the aminotelechelic alternating disiloxane-hydrocarbon polymer of Part 1.

A 250-ml 3-neck round-bottomed flask was fitted with a Dean-Stark trap, condenser, and thermocouple. The reaction was run under nitrogen and stirred magnetically. A mixture of 50 ml N,N-dimethylacetamide, 50 ml of o-xylene and 20 ml of cyclohexane was heated in the flask until 10 ml of the mixture was distilled. The flask was cooled, sealed and transferred to a glovebox. 4,4'-Methylenebis (phenylisocyanate) (MDI, 11.47 gm) was added to the flask. The aminotelechelic alternating disiloxane-hydrocarbon polymer of Part 1 (37.05 gm) was placed in a syringe and transferred to a glovebox. 1,4-Butanediol was also placed in a syringe and transferred to the glovebox. The mixture was heated to 50° C. The aminotelechelic alternating disiloxane-hydrocarbon polymer of Part 1 was added over 15 minutes with the temperature of the mixture kept between 50° C. and 66° C. After the addition was complete, the temperature was maintained at about 65° C. After another 15 minutes, the 1,4-butanediol was added over 5 minutes with the temperature rising to 71° C. The mixture was hazy so additional DMAC was added. After the addition of 58 ml DMAC, the mixture cleared considerably. A drop of dibutyltin dilaurate catalyst was added. The temperature was brought to 90° C. to complete the reaction. Infrared analysis was used to monitor the isocyanate peak for judgement of completion of the reaction. The polymer was precipitated in acetone and water, filtered through bolting cloth and dried in a vacuum oven.

Properties of the polyurethane/urea. The dried polyurethane/urea was heat pressed for testing of mechanical properties. The results are presented in Table 2. Tensile properties of the test specimens were determined using an Instron Testing Machine with crosshead speed of 12.7 cm per minute using a 22.67 kg (50 pound) load cell.

To determine the molecular weights of the polymers, samples were dissolved in tetrahydrofuran and analyzed using an Alliance high performance liquid chromatography system (Waters Technologies Corporation, Milford, Mass.). Phenomenex columns (HR4, 3, 1 and 0.5) were used (Phenomenex USA, Torrance, Calif.). Tetrahydrofuran was used as the eluent at 0.28 ml/min and 50° C. The molecular weight values reported are relative to a polystyrene standard curve.

TABLE 2

| Property | Heat pressed polymer |
| --- | --- |
| Hardness (Shore scale) | 85 A |
| Ultimate tensile | 14.5 MPa (2100 psi) |
| Elongation at break | 410% |
| Young's modulus | 40.7 MPa (5900 psi) |
| Mn | 21500 g/mol |
| Mw | 50000 g/mol |

Example 3

Synthesis of a 700 Mn Aminotelechelic Alternating Siloxane-Hydrocarbon Polymer

A 3-neck round-bottomed flask was fitted with thermometer and adapter, magnetic stirring mechanism, water bath, cold-water condenser, pressure equalized addition funnel, balloon, and stopper. The system was flushed with nitrogen before use. 1,1,3,3-Tetramethyldisiloxane (TMDS, 202.1 gm) was added to the flask. In the addition funnel was placed 1,5-hexadiene (82.06 gm). Catalyst (platinum (divinyltetramethyldisiloxane)) was added dropwise at various points of the reaction as the diene was added dropwise, being careful to control the exotherm of the reaction. The entire reaction took about 1.5 hours, starting at room temperature and reaching a maximum of 59° C.

A 1000-ml 3-neck round-bottomed flask was fitted with thermometer and adapter, magnetic stirring mechanism, heating unit, cold-water condenser, pressure equalized addition funnel, glycerol bubbler, heating mantle, and stopper. The system was flushed with nitrogen during use. N-(Trimethylsilyl)allylamine (107 gm) was added to the flask. Also, toluene (200 ml) was added to the flask. In the addition funnel was placed a portion of the hydride-terminated disiloxane-hydrocarbon polymer from above (178 gm). Catalyst (platinum divinyltetramethyldisiloxane complex) was added intermitently. The flask was heated to 75° C., then the polymer was added over about one hour keeping the temperature between 91° C. and 110° C. Water was added (27 ml). The water was separated. The polymer was rotary evaporated then dried under vacuum.

Example 4

Preparation of a Polyurethane/Urea with a Soft Segment Comprising Alternating Disiloxane/Hydrocarbon Units Fifty grams xylene, 50 grams N,N-dimethylacetamide (DMAC), and 40 milliliters cyclohexane were added to a 3-neck 500-milliliter round-bottomed flask. The flask was outfitted with a Dean-Stark trap, a stirrer powered by an air motor, and a thermocouple. A condenser was connected to the Dean-Stark trap, and an adapter connected to a nitrogen source and bubbler was connected to the condenser. Stirring was initiated and the contents of the flask were heated to 110° C. Nine milliliters of cyclohexane were distilled from the flask. The flask was cooled to 50° C. and the entire apparatus was transferred to a nitrogen-purged glovebox. Then 19.36 grams of flaked MDI were added to the flask. The Dean-Stark trap was then removed and replace with a condenser attached to a drying tube. The mixture in the flask was stirred and 27.61 grams of the aminotelechelic alternating disiloxane-hydrocarbon polymer synthesized in Example 3 was added over ten minutes using a syringe. The rate of addition was controlled in order to keep the contents of the flask at a temperature of less than 50° C. The maximum temperature of the flask during the addition was 49.6° C. Stirring was continued for twenty minutes, then 3.40 grams of 1,4-butanediol was added in one bolus from a 5-cc (cubic centimeter) syringe. The reaction temperature increased from 44° C. to 51° C. over approximately 10 minutes following the addition. After 30 minutes, the polymer had gelled. One hundred grams of DMAC were added to the reaction mixture and it was heated to 110° C., which dissolved the gel. After an additional 30 minutes, there was no isocyanate present by infrared spectroscopy at an absorbance at 2272 cm$^{-1}$. About one gram of additional MDI was added to the reaction flask, and after ten minutes, the product was examined by infrared spectroscopy, which showed no band due to isocyanate. Three more small additions of MDI were made, bringing the amount of MDI in the polymer formulation to a total of 21.52 grams. After the addition of a total of four additions of MDI, a residual isocyanate band was observed by infrared spectroscopy. To bring the isocyanate band to the desired level, an additional 0.25 grams of 1,4-butanediol was added, bringing the total 1,4-butanediol in the formulation to 3.65 grams. An initial attempt to precipitate the polymer by pouring the solution into a Waring blender containing stirred isopropanol was unsuccessful. The polymer was successfully precipitated by pouring the combined DMAC/isopropanol solution into a Waring blender containing stirred acetone. The polymer was then dried overnight in a vacuum oven at 100° C. A portion of the polymer was dissolved in N-methylpyrrolidone and cast into a film. This polymer film was found to have the properties listed in the table below:

TABLE 3

Properties of polyurethane/urea

| Property | |
|---|---|
| Hardness (Shore scale) | 65 D |
| Ultimate tensile strength | 21.4 MPa (3100 psi) |
| Elongation at break | 93% |
| Young's modulus | 244 MPa (35400 psi) |

Example 5

Preparation of a Polyurethane/Urea with a Soft Segment Comprising Alternating Disiloxane/ Hydrocarbon Units One hundred milliliters of toluene, 100 milliliters N,N-dimethylacetamide (DMAC), and 25 milliliters cyclohexane were added to a 3-neck 500-milliliter round-bottomed flask. The flask was outfitted with a Dean-Stark trap, a stirrer powered by an air motor, and a thermocouple. A condenser was connected to the Dean-Stark trap, and an adapter connected to a nitrogen source and bubbler was connected to the condenser. Stirring was initiated and the contents of the flask were heated to 110° C. for two hours. Seven milliliters of cyclohexane were distilled from the flask. The flask was cooled to 50° C. and the entire apparatus was transferred to a nitrogen-purged glovebox. Then 15.94 grams of flaked MDI were added to the flask. The Dean-Stark trap was then removed and replace with a condenser attached to a drying tube. The mixture in the flask was stirred and 30.82 grams of aminotelechelic alternating disiloxane-hydrocarbon polymer was added over five minutes using a syringe, then an additional 2.72 grams of aminotelechelic alternating disiloxane-hydrocarbon polymer synthesized in Example 3 was added over five minutes using a syringe. The maximum temperature of the flask during the addition was 51° C. Stirring was continued for fifteen minutes at 50° C., then 0.84 grams of 1,4-butanediol was added in one bolus from a 5 cc syringe. After three minutes, two drops of stannous octonate catalyst was added, causing an exotherm that reached 54° C. after one minute. After 30 minutes, there was a large isocyanate band in the infrared spectrum. Several portions of the aminotelechelic polymer were added to the reaction mixture, totaling 4.72 grams, but these additions did not change the isocyanate band. It was then assumed that the polymer being formed had poor solubility in the solvent mixture. The mixture was then heated to 70° C., at which point the solution started to bubble. After one minute at this temperature, the mixture thickened and gelled. One hundred additional grams of DMAC were added and the mixture was heated to 110° C. There was no isocyanate band observed at this point, so an additional 0.99 grams MDI was added to the reaction mixture. After the band due to isocyanate had stabilized, the polymer was precipitated in a mixture of isopropanol and water, extracted with acetone, and then dried in a vacuum oven at 100° C. overnight. A portion of the polymer was then redissolved in N-methylpyrrolidone and cast into a film. This polymer film was found to have the properties list in the table below:

TABLE 4

Properties of polyurethane/urea

| Property | |
|---|---|
| Ultimate tensile strength | 33.1 MPa (4800 psi) |
| Elongation at break | 250% |
| Young's modulus | 275 MPa (39900 psi) |

Example 6

Synthesis of a Hydroxytelechelic Alternating Disiloxane-Hydrocarbon Polymer

A 3-necked round-bottomed flask was fitted with thermometer and adapter, magnetic stirring mechanism, water bath, cold-water condenser, pressure equalized addition funnel, balloon, and stopper. The system was flushed with nitrogen before use. 1,1,3,3-Tetramethyldisiloxane (TMDS, 68.0 gm) was added to the flask. In the addition funnel was placed 1,7-octadiene (34.0 gm). Catalyst (platinum (divinyltetramethyldisiloxane)) was added dropwise at various points of the reaction as the diene was added dropwise, being careful to control the exotherm of the reaction. The entire reaction took about 1 hour, starting at room temperature and reaching a maximum of 75° C. Allyloxytrimethylsilane (64.73 gm, AOTMS) was added to the addition funnel. It was added dropwise over about 1 hour with occasional addition of catalyst. Reaction temperature ranged from 30–43° C. Citric acid (0.0570 gm) and methanol (50 ml) were added to the AOTMS terminated polymer (5.32 gm) in hexane (50 ml) in a 250-ml beaker. The solution was washed with deionized water and the solvent removed using a rotary evaporator.

Example 7

Preparation of a Hydroxytelechelic Alternating Disiloxane-Hydrocarbon Polymer

Part 1: Synthesis of 1-acetoxy-11-chlorodimethylsilylundecane.

To a three-liter four-neck round-bottomed flask was charged 1090 grams of 10-undecen-1-yl acetate and 40 drops of (platinum(divinyltetramethyldisiloxane) catalyst solution (2–3% platinum in xylenes). To this mixture was slowly added 425 grams of chlorodimethylsilane from a one-liter addition funnel. The addition took place over 165 minutes, at such a rate to prevent an excessive exotherm. After the initial exotherm, the addition rate was controlled to maintain the temperature of the reaction mixture at about 70° C. A heating mantle was placed under the flask and the reaction mixture was maintained at 34° C. overnight. The crude product was distilled under vacuum directly from the reaction flask, using a distillation column 1.5 cm in diameter and 22 cm in length. The column was packed with stainless steel mesh. On this column was placed a distillation head and a coldfinger. The main cut distilled at about 1 millitorr (0.133 Pa) and 122–125° C. An aliquot was submitted for gas chromatographic analysis to determine purity.

Part 2: Synthesis of an acetoxytelechelic alternating disiloxane-hydrocarbon polymer.

Prior to the reaction, 1,8-bis(chlorodimethyl)octane was distilled under high vacuum (<1 millitorr (0.133 Pa)). The fractions that distilled at about 96° C. were used. The 1-acetoxy-11-chlorodimethylsilylundecane synthesized above (739 grams) and 1,8-bis(chlorodimethylsilyl)octane (663 grams) were combined with one liter of hexanes in a five-liter round-bottomed flask. To this was added 1.38 liters of deionized water. The mixture was stirred magnetically using a poly(tetrafluoroethylene) stirbar. There was a mild exotherm, which peaked at a mixture temperature of 44° C. The mixture was stirred for six days at room temperature. Then the water layer was pumped off the reaction mixture through a glass drop tube using a peristaltic pump. The organic layer was washed twice with a solution of 100 grams sodium carbonate in 1800 milliliters of water. During both washes, the mixture was stirred vigorously for 30 minutes. Then, the organic phase was washed with 1800 milliliters of deionized water for 4–5 times, until the wash water was found to be of neutral pH when tested with pH paper. The organic phase was dried using magnesium sulfate and the hexanes removed using a rotary evaporator.

Part 3: Deprotection of the acetoxytelechelic alternating disiloxane-hydrocarbon polymer to yield a hydroxytelechelic alternating disiloxane-hydrocarbon polymer.

The aceotoxytelechelic alternating disiloxane-hydrocarbon polymer prepared in Part 2 (1234 grams) was placed in a twelve-liter round-bottomed flask with 2.2 liters tetrahydrofuran and 1.9 liters of ethanol. The flask was outfitted with a condenser and the mixture was heated to reflux in the presence of poly(tetrafluoroethylene) boiling chips. Sixty grams of potassium cyanide was weighed into a 400-milliliter beaker and 220 milliliters of deionized water was added. After the potassium cyanide had completely dissolved, the solution was added to the flask over about ten minutes. The reaction was refluxed and turned from a slightly cloudy yellow solution to a clear solution with an orange cast. The pot temperature was 68° C. Analysis by infrared spectroscopy indicated that the product was approximately 44% deprotected. The solvents were removed from the reaction mixture using a rotary evaporator, the crude polymer was redissolved in ethyl ether, and then the crude product was washed four times with water. The washing was performed using a six-liter separatory funnel and each water wash was approximately 1.5 liters. The deprotection step was repeated on the partially deprotected polymer, with the exception that seventy grams of potassium cyanide was used, and the time that the reaction mixture was refluxed was increased to one week.

Additional purification of the hydroxytelechelic alternating disiloxane-hydrocarbon polymer was performed by dissolving the polymer at 50% solids in a 1/1 blend of ether/hexanes. Deionized water washes (1500 ml/wash) were repeated in a 6-liter separatory funnel until they were of neutral pH. Residual water was removed by two treatments of the organic phase with anhydrous magnesium sulfate. After filtration, the solvents were removed by rotary evaporation at 40° C. at 0.1 mm vacuum. The resultant polymer (965.6 grams) was an orange liquid and was determined to be 99.4% deprotected by proton NMR.

The purification procedure was continued by adding an equal volume of anhydrous tetrahydrofuran (Aldrich) to the polymer. The diluted product was passed through an 8.9 cm (3.5 inch) diameter column constructed with layers of glass wool, washed silica sand and 6.4 cm (2.5 inch) of Brockmann 1, neutral, activated alumina (Aldrich). After isolating the first filtrate, the column was rinsed with one liter of fresh tetrahydrofuran. Both of these light-yellow filtrates were processed separately.

The final purification step was a filtration of each filtrate generated in the previous step through a column of Silica gel (Grade 22) covered with an equal quantity of Brockmann 1, neutral, activated alumina. After the polymer solution eluted, the column was rinsed with one liter of fresh tetrahydrofuran. The resultant filtrates were clear and almost colorless. Solvent was removed from each filtrate by rotary evaporation under oil pump vacuum at 40° C. The first filtrate, 517 grams, had a hydroxyl equivalent weight of 520.7 grams/equivalent. The second filtrate, 404 grams, had a hydroxyl equivalent weight of 452.8. The combined yields of the two purified hydroxytelechelic alternating disiloxane-hydrocarbon polymer was 96.4% of the starting deprotected hydroxytelechelic alternating disiloxane-hydrocarbon polymer.

Example 8

Synthesis of a Polyurethane Containing an Alternating Disiloxane-Hydrocarbon Soft Segment Utilizing a One-Step Solution Polymerization Process To a flame-dried, 1-liter, three-neck, round-bottomed flask, 82.95 grams (0.1832 equivalents) hydroxytelechelic alternating disiloxane-hydrocarbon polymer of the previous example and 6.35 grams (0.1411 equivalents) 1,4-butanediol were added. The flask was equipped with air-driven mechanical stirrer with stirrer bearing, a thermocouple with temperature controller, a nitrogen inlet and a nitrogen outlet capped with a mineral oil bubbler to maintain a closed system at atmospheric pressure. All additions took place in a nitrogen-purged glovebox. Anhydrous 1,4-dioxane (Aldrich, 400 grams) was added to make a clear, low-viscosity solution. A slight nitrogen purge was introduced into the headspace of the flask while the stirred contents were heated to 90° C. When the reaction mixture reached this temperature, 41.92 grams (0.3340 equivalents) of solid, flaked MDI (fused Mondur M, Bayer Corporation) was added. The reaction mixture exotherm reached 98° C. After the exotherm was complete, the reaction mixture was maintained at 90° C. Infrared analysis of the polymer solution determined that the reaction was progressing slowly as shown by FTIR analysis, which indicated a significant isocyanate absorbance at 2270 cm$^{-1}$. After 5.5 hours, two drops of tin(II) 2-ethylhexanoate catalyst (Aldrich) was added to increase the rate of polymerization. Following the catalyst addition, the viscosity increased very rapidly and additional anhydrous dioxane was added to reduce the solids content from 25 to 20 percent in order to lower the viscosity. Infrared analysis revealed the reaction was complete and a relatively weak band due to residual isocyanate was detected using FTIR. This was expected by the reaction stoichiometry, which was calculated to produce an isocyanate-terminated polyurethane. The viscous dioxane/polymer solution was poured into isopropanol as it was rapidly stirred in a 1.2 liter glass container by a variable speed, explosion proof laboratory blender. The result was a homogeneous, viscous polymer solution with a one to two blend of dioxane/isopropanol. Deionized water was slowly added to precipitate the polymer as a coarse powder. The solidified polymer was filtered from the solvent and returned to the blender assembly twice to be blended, washed and filtered with methanol to selectively remove the majority of the dioxane. The resultant polymer was dried in a vacuum oven for 60 hours at 50° C. followed by 24 hours at 80° C. The white powder was compression molded at 210° C. with a Carver press into clear 0.635 mm (25 mil) films. After annealing at 70° C. for 24 hours, mechanical properties were measured with an MTS Sintech I/D using ASTM D638-5 method, with extensometer. Results were as follows: Ultimate Tensile Strength=30.2 MPa (4378 psi), Elongation at break=606% and Young's Modulus=57.9 MPa (8399 psi). Infrared analysis detected absorbencies at 3327, 2964, 2915, 2847, 1713, 1695, 1596, 1540, 1525, 1466, 1412, 1312, 1257, 1237, 1063, 1045, 844, and 795 cm$^{-1}$.

Example 9

Synthesis of a Polyurethane Containing an Alternating Disiloxane-Hydrocarbon Soft Segment Utilizing a One-Step, Solvent-Free Polymerization Process Synthesis was completed in a nitrogen-purged glovebox utilizing the same lots of reactants as in Example 8. In a 250 ml polypropylene beaker, 82.96 grams (0.1832 equivalents) hydroxytelechelic alternating disiloxane-hydrocarbon polymer was blended with 6.36 grams (0.1411 equivalents) of 1,4-butanediol. The homogenous diol blend was heated to 100° C. in an oven located in a nitrogen-purged glovebox. Next, 40.95 grams (0.3259 equivalents) of clear, precipitate free, molten MDI was added. The clear, low viscosity blend was stirred rapidly with a polypropylene stir stick in the absence of any catalyst. After 30 seconds, the blend became opaque and viscosity rapidly increased. After 60 seconds, the partially reacted polymer was too viscous to stir. The stirrer stick was removed and the reaction was further heated in the glovebox oven for 18 hours at 100° C. After cooling to room temperature, the beaker was removed and the solid polymer was cut into pieces with a band saw. Polymer films were compression molded at 210° C. with a Carver press into slightly hazy 0.635 mm (25 mil) films. After annealing at 70° C. for 24 hours, mechanical properties were measured using ASTM D638-5 method, with a MTS Sintech I/D with extensometer. Results were as follows: Ultimate Tensile Strength=26.3 MPa (3418 psi), Elongation at break=610% and Young's Modulus=57.8 MPa (8389 psi). Infrared analysis of a 0.08 mm (3 mil) thick, molded film detected a very small level of residual isocyanate at 2270 cm$^{-1}$, as expected from the reaction stoichiometry. In general, the infrared spectrum had the same spectral features as the solution-polymerized polymer of Example 8.

Example 10

Synthesis of a Polyurethane Containing an Alternating Disiloxane-Hydrocarbon Soft Segment Utilizing a Two-Step, Solvent-Free Polymerization This polymer was made with the same reactants as in Examples 8 and 9. In a nitrogen purged dry box, 12.77 grams (0.02823 equivalents) hydroxytelechelic alternating disiloxane-hydrocarbon polymer was preheated in a 250 ml polypropylene beaker to 100° C. in the dry box oven before 6.32 grams (0.05036 equivalents) of solid, flaked MDI was added. The reactants were rapidly stirred with a polypropylene stir stick to form a clear, low viscosity solution before returning the beaker to the 100° C. oven. After 10 minutes, the isocyanate-terminated prepolymer was a clear, medium viscosity blend. After 30 minutes, there was no further increase in viscosity. In the absence of any catalyst, 0.98 grams (0.02178 equivalents) of 1,4-butanediol was added. After stirring for 2 minutes, the medium viscosity blend went from clear to hazy. After 4 minutes, the blend was too viscous to stir and reaction blend was heated for 18 hours at 100° C. in the dry box oven to complete the reaction. After cooling to room temperature, the beaker was removed and the solid polymer was cut into pieces with a band saw. Polymer films were compression molded at 220° C. in a Carver press into 0.635 mm (25 mil) films. After annealing for 24 hours at 70° C., mechanical properties were measured using ASTM D638-5 method with an MTS Sintech I/D with extensometer. Results were as follows: Ultimate Tensile Strength=23.9 MPA (3468 psi), Elongation at break=560%, Young's Modulus=53.3 MPa (7736 psi). Gel Permeation Chromatography (GPC) molecular weight in tetrahydrofuran utilizing polystyrene standards determined that Mw=101,000, Mn=42,300, polydispersivity=2.40. Differential Scanning Calorimeter (DSC) was used to determine $T_g$=−73° C., $T_m$=83, 137& 166° C. and $T_c$=47° C. FTIR spectrum of a 0.08 mm (3 mil) thick molded film had the same spectral features as the polyurethanes described in Examples 8 and 9. The polymer had a residual isocyanate band detected at 2270 cm$^{-1}$, as expected by the reaction stoichiometry.

Example 11

Stability Testing

The chemical stability of the polyurethanes synthesized in Examples 8 and 9 were compared to polyurethane and silicone polymers that are standards of the medical industry for use in long-term implant applications, such as pacemaker leads. In the Tables below, PELLETHANE 80A refers to PELLETHANE-2363-80A, a polyether polyurethane sold by the Dow Chemical Company, Midland, Mich.; ELASTHANE 55D is a polyether polyurethane sold by Polymer Technologies Group, Berkeley, Calif.; and the silicones MED-4516 and MED-4719 are sold by Nusil Technology, Carpinteria, Calif. Polymer specimens were soaked in various solutions to test their oxidative and hydrolytic stability. The solutions used include 1 N aqueous sodium hydroxide, 1 N aqueous hydrochloric acid, 1 M silver nitrate, and 1 M ferric chloride. The polymers were molded into 0.635 mm (25 mil) thick films and cut into test specimens with a die according to ASTM D638-5. Test specimens were stored at 70° C. for 4 and 8 weeks in each of these solutions. For each test point, 5–8 specimens were added to each 100-ml (four-ounce) jar of solution. Tensile properties of the test specimens were determined using a MTS Sintech 1/D tensile tester with extensometer with a crosshead speed of 12.7 cm per minute using a 22.67 kg (50 pound) load cell. Retention of physical properties was determined by comparison of the tensile properties of the test specimens to the tensile properties of identical specimens stored at ambient laboratory conditions. This comparison is reported as a percentage in the Tables as "percentage of properties retained". The specimens were tested both wet and dry. A "wet" specimen is one removed from the test solution, rinsed with deionized water, blotted dry, and tested immediately. A "dry" specimen is tested after rinsing with deionized water, drying to a constant weight in a vacuum oven, and then allowing the moisture level of the specimen to equilibrate to ambient laboratory conditions. In these Tables, "UTS" refers to ultimate tensile strength and % E refers to percent elongation.

TABLE 5

| PELLETHANE 80A - Percentage of properties retained | | | | | |
|---|---|---|---|---|---|
| | 4 Weeks (Wet) | | 8 Weeks (wet) | | 8 Weeks (Dry) | |
| Conditions | UTS | % E | UTS | % E | UTS | % E |
| NaOH | 91 | 113 | 94 | 120 | 115 | 120 |
| HCl | 74 | 97 | 69 | 108 | 94 | 115 |

TABLE 5-continued

PELLETHANE 80A - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| FeCl$_3$ | 68 | 128 | 40 | 119 | 48 | 105 |
| AgNO$_3$ | 23 | 99 | 30 | 117 | 46 | 108 |

TABLE 6

ELASTHANE 55D - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| NaOH | 95 | 114 | 101 | 123 | 117 | 126 |
| HCl | 90 | 106 | 82 | 115 | 99 | 118 |
| FeCl$_3$ | 83 | 118 | 64 | 114 | 69 | 88 |
| AgNO$_3$ | 57 | 104 | 29 | 83 | 41 | 80 |

TABLE 7

Polymer of Example 8 - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| NaOH | 75 | 106 | 65 | 99 | 79 | 101 |
| HCl | 74 | 119 | 59 | 117 | 77 | 124 |
| FeCl$_3$ | 74 | 106 | 70 | 117 | 84 | 114 |
| AgNO$_3$ | 69 | 97 | 57 | 89 | 67 | 93 |

TABLE 8

Polymer of Example 9 - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| NaOH | 75 | 90 | 66 | 93 | 71 | 86 |
| HCl | 68 | 110 | 61 | 109 | 81 | 121 |
| FeCl$_3$ | 73 | 106 | 64 | 107 | 83 | 119 |
| AgNO$_3$ | 70 | 90 | 63 | 89 | 73 | 89 |

TABLE 9

MED-4516 Silicone Elastomer - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| NaOH | 93 | 79 | 97 | 76 | 99 | 78 |
| HCl | 43 | 49 | 38 | 38 | 44 | 38 |
| FeCl$_3$ | 83 | 84 | 70 | 67 | 71 | 70 |
| AgNO$_3$ | 91 | 84 | 89 | 84 | 86 | 76 |

TABLE 10

MED-4719 Silicone Elastomer - Percentage of properties retained

| Conditions | 4 Weeks (Wet) | | 8 Weeks (wet) | | 8 Weeks (Dry) | |
|---|---|---|---|---|---|---|
| | UTS | % E | UTS | % E | UTS | % E |
| NaOH | 118 | 73 | 107 | 114 | 126 | 68 |
| HCl | 28 | 42 | 23 | 26 | 25 | 23 |
| FeCl$_3$ | 46 | 52 | 33 | 42 | 38 | 44 |
| AgNO$_3$ | 111 | 78 | 103 | 125 | 105 | 72 |

It can be seen from the data presented in Tables 5–10 that the polyether polyurethanes (Tables 5 and 6) are more susceptible to oxidative degradation than the polymers of the present invention (Tables 7 and 8). It can also be seen from the data above that the silicones (Tables 9 and 10) are more susceptible to acidic and basic hydrolysis than the polymers of the present invention. It has thus been demonstrated that the polymers of the present invention have greater resistance to oxidative attack than the polyurethanes commonly used to fabricate medical devices, and that the polymers of the present invention have greater resistance to hydrolysis than the silicones commonly used to fabricate medical devices. Thus, the polymers of the present invention have a combined resistance to oxidative and hydrolytic attack that is not found in the polymers currently used to fabricate medical devices intended for long-term implant applications.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A polymer comprising urethane linkages and one or more silicon-containing groups, wherein the polymer is derived from a compound of the formula:

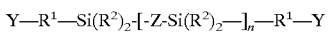

$$Y-R^1-Si(R^2)_2-[-Z-Si(R^2)_2-]_n-R^1-Y$$

wherein:
  each Y is independently OH or NR$^4$H;
  n=2 or more;
  each R$^1$ is independently a straight chain or branched alkylene group optionally including heteroatoms;
  each R$^2$ is independently a saturated or unsaturated aliphatic group, an aromatic group, or combinations thereof, optionally including heteroatoms;
  Z is oxygen or R$^3$, wherein each R$^3$ is independently a straight chain alkylene group, a phenylene group, or a straight chain or branched alkyl substituted phenylene group, wherein each R$^3$ optionally includes heteroatoms; and
  each R$^4$ is independently H or a saturated or unsaturated aliphatic group, an aromatic group, or combinations thereof;
with the proviso that at least one of the Z groups is oxygen and at least one of the Z groups is R$^3$; and
with the proviso that R$^1$ does not include urethane groups when Y is OH; and further with the proviso that the polymer is substantially free of ester linkages.

2. The polymer of claim 1 wherein n=2 to 50.

3. The polymer of claim 1 wherein each $R^1$ is independently a straight chain or branched (C3–C20)alkylene group.

4. The polymer of claim 1 wherein each $R^2$ is independently a straight chain or branched (C1–C20)alkyl group.

5. The polymer of claim 4 wherein each $R^2$ is independently a straight chain or branched (C1–C3)alkyl group.

6. The polymer of claim 1 wherein each $R^2$ is independently a phenyl group or a straight chain or branched (C1–C20)alkyl substituted phenyl group.

7. The polymer of claim 6 wherein each $R^2$ is independently a phenyl group or a straight chain or branched (C1–C6)alkyl substituted phenyl group.

8. The polymer of claim 1 wherein each $R^3$ is independently a straight chain (C1–C20)alkylene group.

9. The polymer of claim 8 wherein each $R^3$ is independently a straight chain (C4–C12)alkylene group.

10. The polymer of claim 9 wherein each $R^3$ is independently a straight chain (C6–C10)alkylene group.

11. The polymer of claim 1 wherein each $R^3$ is independently a phenylene group or a straight chain or branched (C1–C20)alkyl substituted phenylene group.

12. The polymer of claim 1 wherein each $R^3$ is independently a phenylene group or a straight chain or branched (C1–C6)alkyl substituted phenylene group.

13. The polymer of claim 1 wherein each Y is OH.

14. The polymer of claim 1 wherein each $R^4$ is independently H or a straight chain alkyl group.

15. The polymer of claim 1 which is a segmented polyurethane.

16. The polymer of claim 1 which is a biomaterial.

17. The polymer of claim 1 which is substantially free of ether, ester, and carbonate linkages.

18. The polymer of claim 1 which is linear, branched, or crosslinked.

19. The polymer of claim 1 wherein every other Z is oxygen.

20. The polymer of claim 1 further comprising one or more soft segments derived from a diol that does not contain a silicon-containing group.

21. The polymer of claim 1 further comprising one or more hard segments derived from a chain extender.

22. The polymer of claim 1 which is resistant to oxidation and/or hydrolysis.

23. The polymer of claim 1 which has a number average molecular weight of at least about 20,000 g/mole.

24. A polymer comprising urethane linkages and one or more silicon-containing groups, wherein the polymer is derived from a compound of the formula:

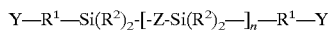

wherein:
each Y is $NH_2$;
n=2 or more;
each $R^1$ is independently a straight chain or branched alkylene group optionally including heteroatoms;
each $R^2$ is independently a saturated or unsaturated aliphatic group, an aromatic group, or combinations thereof, optionally including heteroatoms;
Z is oxygen or $R^3$, wherein each $R^3$ is independently a straight chain alkylene group, a phenylene group, or a straight chain or branched alkyl substituted phenylene group, wherein each $R^3$ optionally includes heteroatoms; and each $R^4$ is independently H or a saturated or unsaturated aliphatic group, an aromatic group, or combinations there of;
with the proviso that at least one of the Z groups is oxygen and at least one of the Z groups is $R^3$; and
with the proviso that $R^1$ does not include urethane groups when Y is OH.

25. A polymer comprising urethane linkages and one or more silicon-containing groups, wherein the polymer is not crosslinked and comprises a group of the formula:

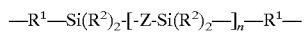

wherein:
n=2 or more;
each $R^1$ is independently a straight chain or branched alkylene group optionally including heteroatoms;
each $R^2$ is independently a saturated or unsaturated aliphatic group, an aromatic group, or combinations thereof, optionally including heteroatoms;
Z is oxygen or $R^3$, wherein each $R^3$ is independently a straight chain alkylene group, a phenylene group, or a straight chain or branched alkyl substituted phenylene group, wherein each $R^3$ optionally includes heteroatoms; and
with the proviso that at least one of the Z groups is oxygen and at least one of the Z groups is $R^3$; and
with the proviso that $R^1$ does not include urethane groups; and further
with the proviso that the polymer is substantially free of ester linkages.

26. A method of making a segmented polymer comprising urethane linkages, the method comprising: combining a polyisocyanate with a compound of the formula:

wherein:
each Y is independently OH or $NR^4H$;
n=2 or more;
each $R^1$ is independently a straight chain or branched alkylene group optionally including heteroatoms;
each $R^2$ is independently a saturated or unsaturated aliphatic group, an aromatic group, or combinations thereof, optionally including heteroatoms;
Z is oxygen or $R^3$, wherein each $R^3$ is independently a straight chain alkylene group, a phenylene group, or a straight chain or branched alkyl substituted phenylene group, wherein each $R^3$ optionally includes heteroatoms; and
each $R^4$ is independently H or a saturated or unsaturated aliphatic group, an aromatic group or combinations thereof;
with the proviso that at least one of the Z groups is oxygen and at least one of the Z groups is $R^3$;
with the proviso that $R^1$ does not include urethane groups when Y is OH; and further
with the proviso that the polymer is substantial free of ester linkages.

27. A polymer comprising urethane linkages and one or more silicon-containing groups, wherein the polymer is derived from a compound of the formula:

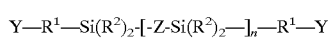

wherein:
  each Y is independently OH or NR⁴H;
  n=2 or more;
  each $R^1$ is independently a straight chain or branched alkylene group optionally including heteroatoms;
  each $R^2$ is independently a saturated or unsaturated aliphatic group, an aromatic group, or combinations thereof, optionally including heteroatoms;
  Z is oxygen or $R^3$, wherein each $R^3$ is independently a straight chain alkylene group, a phenylene group, or a straight chain or branched alkyl substituted phenylene group; and
  each $R^4$ is independently H or a saturated aliphatic group;
  with the proviso that at least one of the Z groups is oxygen and at least one of the Z groups is $R^3$; and
  with the proviso that $R^1$ does not include urethane groups when Y is OH; and further
  with the proviso that the polymer is substantially free of ester linkages.

28. A polymer comprising urethane linkages and one or more silicon-containing groups, wherein the polymer is not crosslinked and comprises a group of the formula:

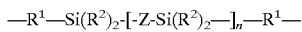

wherein:
  n=2 or more;
  each $R^1$ is independently a straight chain or branched alkylene group optionally including heteroatoms;
  each $R^2$ is independently a saturated or unsaturated aliphatic group, an aromatic group, or combinations thereof, optionally including heteroatoms;
  Z is oxygen or $R^3$, wherein each $R^3$ is independently a straight chain alkylene group, a phenylene group, or a straight chain or branched alkyl substituted phenylene group;

with the proviso that at least one of the Z groups is oxygen and at least one of the Z groups is $R^3$; and
with the proviso that $R^1$ does not include urethane groups; and further
with the proviso that the polymer is substantially free of ester linkages.

29. A method of making a segmented polymer comprising urethane linkages, the method comprising: combining a polyisocyanate with a compound of the formula:

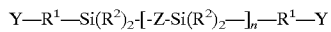

wherein:
  each Y is independently OH or NR⁴H;
  n=2 or more;
  each $R^1$ is independently a straight chain or branched alkylene group optionally including heteroatoms;
  each $R^2$ is independently a saturated or unsaturated aliphatic group, an aromatic group, or combinations thereof, optionally including heteroatoms;
  Z is oxygen or $R^3$, wherein each $R^3$ is independently a straight chain alkylene group, a phenylene group, or a straight chain or branched alkyl substituted phenylene group; and
  each $R^4$ is independently H or a saturated aliphatic group;
  with the proviso that at least one of the Z groups is oxygen and at least one of the Z groups is $R^3$; and
  with the proviso that $R^1$ does not include urethane groups when Y is OH; and further
  with the proviso that the polymer is substantially free of ester linkages.

* * * * *

UNITED STATES PATENT AND TRADEMARK OFFICE
CERTIFICATE OF CORRECTION

PATENT NO. : 6,984,700 B2
DATED : January 10, 2006
INVENTOR(S) : Benz et al.

It is certified that error appears in the above-identified patent and that said Letters Patent is hereby corrected as shown below:

<u>Column 24,</u>
Line 61, delete "substantial" and replace with -- substantially --.

Signed and Sealed this

Eighteenth Day of April, 2006

JON W. DUDAS
*Director of the United States Patent and Trademark Office*